United States Patent [19]
Levy

[11] Patent Number: 5,292,000
[45] Date of Patent: Mar. 8, 1994

[54] HOLDER FOR MEDICAL SPECIMEN SLIDE

[76] Inventor: Abner Levy, 325 N. Oakhurst Dr., P4, Beverly Hills, Calif. 90210

[21] Appl. No.: 975,878

[22] Filed: Nov. 13, 1992

[51] Int. Cl.$^5$ .............................................. B65D 85/48
[52] U.S. Cl. ............................ 206/456; 206/45.31
[58] Field of Search ............................ 206/456, 45.31

[56] References Cited

U.S. PATENT DOCUMENTS

| | | | |
|---|---|---|---|
| 3,215,332 | 11/1965 | Bess | 206/456 |
| 3,710,975 | 1/1973 | Jansen | 206/456 X |
| 4,819,804 | 4/1989 | Levy | 206/456 |
| 5,147,042 | 9/1992 | Levy | 206/456 |

Primary Examiner—William I. Price
Attorney, Agent, or Firm—Beehler & Pavitt

[57] ABSTRACT

A holder for packaging a biological specimen slide is heat formed from a single sheet of plastic, with tray and cover portions foldable to a closed condition along a hinge line. A window opening in the cover portion allows viewing of identification markings on a slide in the closed holder. The window is initially closed by an integrally formed push-out panel which is removed upon use of the holder as a flag of previous usage of the holder to prevent its unintentional reuse.

10 Claims, 2 Drawing Sheets

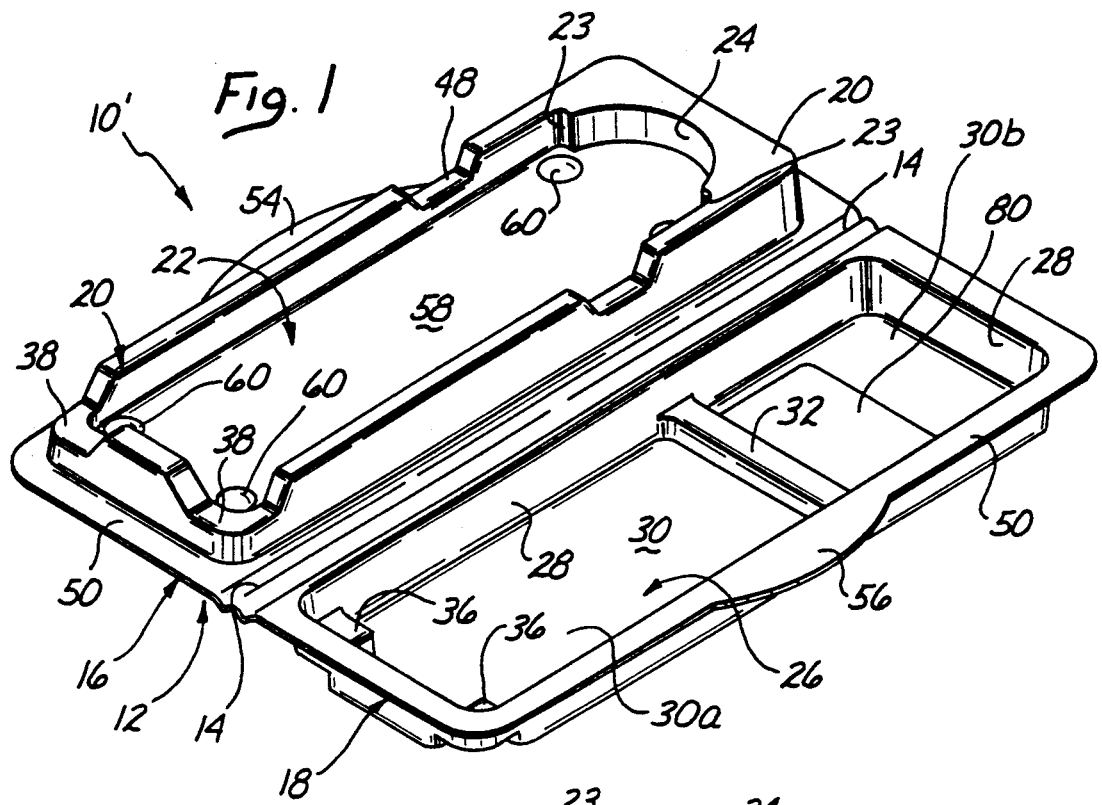
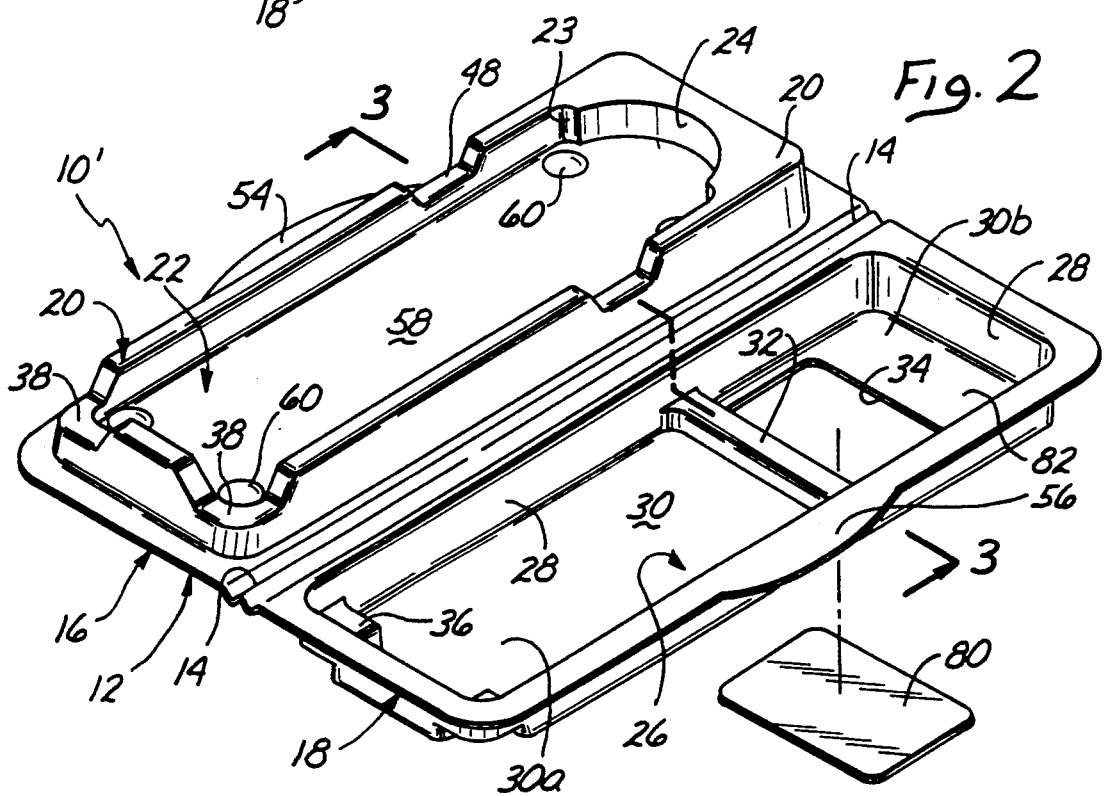

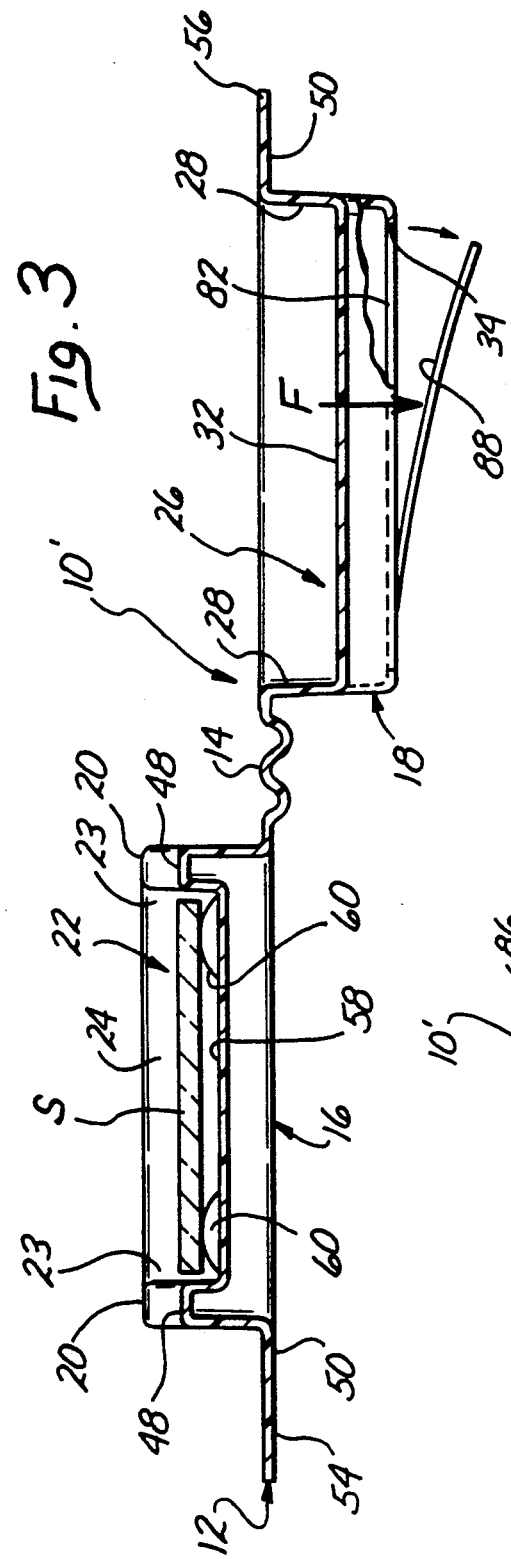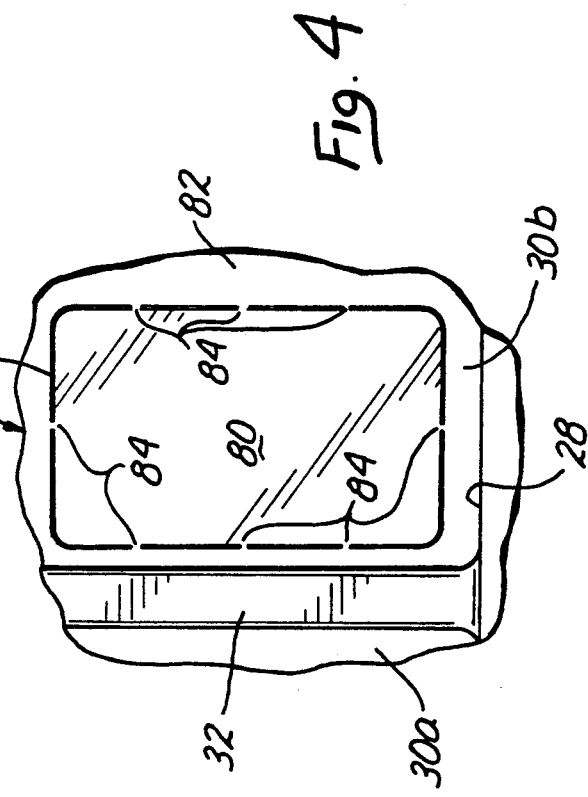

HOLDER FOR MEDICAL SPECIMEN SLIDE

BACKGROUND OF THE INVENTION

1. Field Of The Invention

The present invention relates to the field of medical disposables, and in particular to holders for slides used for conveying samples of biological tissues or fluids for laboratory analysis. The use of slides for this purpose is widespread not only in the medical and biological fields, but also in chemical and related analytical and experimental problem.

2. Background Of The Invention

The use of specimen slides, typically consisting of thin rectangular sheets of glass, for the collection, packaging and storage of biological specimens has prompted the design and fabrication of small, inexpensive, disposable packets and holders of various types, designs and materials. These items are intended to protect the relatively fragile glass slide and to preserve the specimen smeared or deposited on the slide against contamination or physical damage. Such packaging allows the specimen slide to be handled, stored and transported in a convenient and dependable manner until the specimen is processed, in the laboratory or otherwise.

U.S. Pat. No. 5,147,042 granted to this applicant discloses an improved medical specimen slide holder which facilitates and expedites the handling of both the slide and the package by all personnel involved in the specimen collection and specimen analysis procedures, while at the same time enhancing the level of protection afforded to both the specimen and the slide. The patented holder has a tray portion and a cover portion, a ridge defining a slide receiving recess in the tray portion, the cover portion being configured and dimensioned to make a friction fit with the ridge in a closed condition of the holder, and has a window in at least one of the portions for exposing to view an identification bearing portion of the slide in the closed condition of the slide holder. The window allows easy reading of the identifying indicia or markings typically written at one end of the slide by the person taking the sample to reference the biological sample to a particular patient or source. It therefore becomes unnecessary to open the holder package in order to view these identifying markings, which expedites the physical handling of the package and reduces the possibility of damage, contamination or loss of the slide and specimen.

The entire slide holder may be molded of a single sheet of thermoplastic material for low cost large volume production and for ease of use and handling.

The specimen slide holder of U.S. Pat. No. 5,147,042 is intended for single use only, after which it should be discarded. The slide holder is likely to become contaminated with microorganisms present in the environment and also with material from the specimen on the slide. Thus, if the slide holder is reused, a subsequent specimen can become contaminated with material from a previous specimen or microorganisms accumulated on the slide holder, thus leading to an erroneous diagnosis and misleading laboratory test results. This is of course undesirable and potentially dangerous to patients, and is a result to be avoided insofar as possible.

What is needed therefore is a slide holder which can provide a clear, unambiguous and positive indication of prior usage to the physician who will therefore not be mislead into using a potentially contaminated slide holder. The indication of prior use should be such that it cannot be returned to an original condition indicative of an unused slide holder without great difficulty.

While the slide holder disclosed in U.S. Pat. No. 5,147,042 works well for its intended purpose, it can be further improved to supply a clearly visible, unambiguous and positive indication or flag of prior usage of the slide holder at no significant increase in cost of the disposable slide holder, thereby to prevent unintentional reuse of a used and possibly contaminated slide holder.

This improvement is accomplished by providing a panel which in an original condition of the slide holder is integral with the holder and closes the window. The panel is attached to the slide holder by a tear line consisting of relatively weak connecting links or equivalent means which are preferentially rupturable when manual force is applied to the panel, allowing easy detachment and removal of the panel and consequent opening of the window.

As the panel is initially integrally part of the sheet of material from which the slide holder is molded, it adds no additional cost or complexity to the manufacturing process or to the product. The improvement simply involves providing a weakened connection between the panel and the rest of the slide holder, so as to retain the panel in the window, rather than simply stamping out and discarding the panel during original manufacture of the slide holder.

The panel readily breaks away from the slide holder when pushed, as by a finger pressing on the panel, either from the inside or outside of the slide holder. Typically, the physician taking the specimen would push out the panel from the inside of the slide holder, while the slide holder is still open for receiving the specimen slide. Once the panel is broken out, the open window serves as a positive indication of prior use of the holder, and alerts all subsequent persons coming into possession of the slide holder to the fact of its prior usage. The open window provides all the benefits already summarized above, allowing easy inspection of the identification indicia on the slide without having to open the slide holder which might subject the slide to the risk of falling and breakage, or smearing and contamination of the specimen.

These and other features and advantages of the present invention will be better understood by reference to the following detailed description of the preferred embodiments and the attached drawings.

BRIEF DESCRIPTION OF THE DRAWINGS

FIG. 1 is a perspective view of the improved slide holder in its original condition with the window closed by the break-away panel;

FIG. 2 is a view as in FIG. 1, showing the open window after detachment of the panel;

FIG. 3 is a section taken along line 3—3 in FIG. 2 showing the panel partially detached from the slide holder;

FIG. 4 is a fragmentary top plan view of the interior side of the cover portion of the slide holder, showing the panel attached to the cover portion in the original condition of the slide holder as in FIG. 1.

DETAILED DESCRIPTION OF THE PREFERRED EMBODIMENTS

With reference to the attached drawings, FIG. 1 shows a medical specimen slide holder 10 according to this invention. All features of the slide holder 10 shown in the drawings and described below can be formed on a base sheet 12 as an integral unit in a single heat forming and die cutting step from thin thermoplastic sheet material. The base sheet 12 is divided by a hinge line 14 into a tray portion 16 and a cover portion 18. A peripheral flange 50 encompasses both the tray portion 16 and cover portion 18 and defines the plane of the base sheet 12 from which the three dimensional features described above are molded. This is best understood by reference to FIG. 3, which shows the three dimensional forming of the originally planar base sheet 12, and in particular illustrates the deformation of base sheet plane in mutually opposite directions.

A ridge 20 on the tray portion 16 defines a generally tray recess 22 which is shaped and dimensioned to receive a specimen slide S as shown in FIG. 3. One end of the tray recess is defined by end surfaces 23, and an arcuate cove 24 between the end surfaces 23 allows a fingertip to engage the edge of the slide S in order to lift the slide out of the tray recess.

The ridge 20 rises on the base sheet 12 as a male structure one side of the hinge line 14, while the cover portion 18 is molded to form female shell 52 projecting downwardly from the base sheet on the opposite side of the hinge line 14. The shell 52 fits closely about and makes retentive frictional engagement with the ridge 20 to hold tray portion 16 and cover portion 18 in the closed condition shown in FIGS. 3 and 4 of U.S. Pat. No. 5,147,042, and also to provide a substantial seal of the interior of the closed holder 10.

The concave side of the shell forms a rectangular cavity 26, with a side wall 28 and an internal surface or bottom 30 which overlies the slide in the tray recess 22. The interior of the shell cavity 26 is divided into sections 30a and 30b by a ridge partition 32 which rises from the inner surface 30 to a height somewhat greater than one third the height of the side wall 28, and extends the full width of the cavity transversely to the hinge line 14. A rectangular window opening 34 is cut into the section 30b of the cover bottom 30, adjacent to the partition 32. The cover portion 18 also features two corner blocks 36 which rise to the same height as the partition 32 in the cover shell cavity 26.

The ridge 20 of the tray portion 16 has a pair of corner notches 38 and two side notches 48 which respectively admit the corner blocks 38 and the partition 32 of the cover portion 18, when the holder 10 is folded along the hinge line 14 to its closed condition.

FIG. 3 shows that the ridge 20 is hollow on its underside and is created by deformation of the base sheet in a suitable forming die. This forming die preferably also forms a pair of tabs 54 and 56 which extend from opposite free edges of the holder 10 as shown in FIGS. 1 and 2. When the holder 10 is folded to the closed condition, the two tabs are joined in overlying relationship, with the lower tab 54 projecting somewhat beyond the edge of the upper tab 56. This facilitates manual separation of the two tabs which can then be pulled apart to open the package 10 for access to its interior.

FIG. 3 shows a typical medical specimen slide S placed in the tray recess 22 of the slide holder 10. Four slide spacer elements 60 in the form of small rounded bumps rise from the tray bottom 58 and support slide S away from contact with the tray bottom. The spacer elements 60 are positioned so as to contact marginal areas of the slide, in this case near the four corners of the slide, to avoid contact with more central, specimen bearing portions of the slide. In the closed condition of the holder 10 the corner blocks 36 extend into the tray recess 22 opposite the spacer elements 60 adjacent the corner notches 38. The height of the spacer elements 60 on the tray portion, and the partition 32 and corner blocks 36 on the cover portion 18 are such as to hold the slide S substantially clamped therebetween as shown in FIGS. 3 and 4 of U.S. Pat. No. 5,147,042, in spaced relationship and away from contact with both the tray bottom 58 and the cover bottom 30, to avoid smearing of the specimen against the interior surfaces of the holder package 10.

The improved slide holder here disclosed differs from the slide holder 10 of U.S. Pat. No. 5,147,042 in that the window 34 is closed by a break-away or push-out panel 80 in an original condition of the improved slide holder.

FIG. 4 shows in plan view the interior of the cover portion 18 in the original condition of the holder 10 with the push out panel 80 attached to the cover top 82 by links 84 spaced along a rectangular cut 86. The links 84 bridge the cut 86 and connect the panel 80 to the cover top 82 to form a tear line in the original condition of the slide holder 10. The links 84 are sufficiently small in number and in width so that the links rupture preferentially to either the panel 80 or the cover top 82 when sufficient manual force is applied against the panel 80 relative to the cover top 82. The rectangular cut 86 and connecting links 84 are readily formed by use of a suitable die to cut through the sheet 12, in a manner known to those possessed of ordinary skill in the art, preferably with the same forming die used in forming the entire holder 10.

The panel 80 breaks away when a finger is applied against the panel, to either its interior or exterior surface, and the finger is pushed through the window 34.

FIG. 3 illustrates the panel 80 partially broken away from cover 16 in response to a manual force F applied to its interior surface 88. FIG. 2 shows the panel 80 fully detached from the slide holder 10, and the window 36 open as a result. In the condition of FIG. 7 with the panel 80 detached from the slide holder 10, the slide holder 10 becomes similar to the slide holder of U.S. Pat. No. 5,147,042, with all the benefits and advantages associated with the window opening 34.

In the event that the panel 80 does not fully break away along all four sides from the cover top 82, then the partially detached panel 80 can be grasped between two fingers on the exterior of the slide holder 10 and pulled away until fully detached from the slide holder. The panel 80 is then discarded.

A statement may be printed on the slide holder, preferably on the panel 80 itself, as a reminder to the technician or physician using the slide holder that panel 80 should be removed. Words such as "PUSH OUT", may serve this purpose. This statement may be embossed as raised lettering formed in the thermoplastic molding process by which the slide holder 10 is made, by suitable modification of the forming die.

Users of slide holders are educated to this novel feature of the improved slide holder 10 through literature accompanying the original unused slides. The users are therefore aware that a slide holder with an open window 34 is not to be used, as the removal of the panel 80 is indicative of prior handling of the slide holder and possible prior use of the article for transport of a biological specimen. The push out panel 80 therefore provides an inexpensive and convenient means for flagging red slide holders in a reliable manner. It is quite difficult, if not impossible to reattach the panel 80 to the slide holder in a non-obvious manner without considerable effort. Yet, the improved slide holder 10 can be manufactured at a cost essentially similar to that of the slide holder 10 of FIGS. 1–5 without this flagging feature, an important consideration given the disposable nature of this article.

While a particular embodiment of the invention has been shown and illustrated for purposes of clarity and example, it must be understood that many changes, substitutions and modifications to the described embodiment will be apparent to those possessed of ordinary skill in the art without departing from the scope and spirit of the present invention which is defined by the attached claims.

What is claimed is:

1. A holder for a specimen slide of substantially rectangular shape and having a top surface including an identification bearing portion and a specimen bearing portion of said top surface, said holder comprising:
   a tray portion defining a slide receiving recess having a tray bottom surface and a cover portion having a cover top surface:
   said cover portion configured and dimensioned to retentively engage said tray portion in a closed condition of said holder; and
   a window defined in at least one of said tray bottom and cover top for exposing to view said identification bearing portion of a said slide in said closed condition;
   said window being closed in an original condition of said holder by a panel attached to said least one of said tray bottom and cover top by supporting means, said supporting means being preferentially rupturable under manual force applied to said panel for removing said panel and opening said window.

2. The holder of claim 1 further comprising spacer means on both said portions for supporting the slide in spaced relationship with said tray bottom and cover top.

3. The holder of claim 2 wherein said spacer means comprise partition means on said least one of said portions adapted to bear against the slide and thereby limit exposure of said specimen bearing portion of the slide to said window opening.

4. The holder of claim 2 wherein said tray and cover portions, said spacer means, said panel and said supporting means are unitarily formed by vacuum molding of a single sheet of thermoplastic material, said tray and cover portions being joined along a hinge line in said single sheet.

5. A unitary holder for a medical specimen slide comprised of a single thin sheet molded into a three dimensional structure wherein said sheet retains a substantially uniform thickness throughout said holder, said sheet divided along a hinge line into a tray portion and a cover portion and having a peripheral flange defining a base plane in an open condition of said holder:
   a male ridge structure rising above said plane on said tray portion, said ridge structure defining a tray recess including a tray bottom dimensioned to receive the specimen slide;
   a concave shell including a cover top formed below said plane in said cover portion, said shell adapted to retentively engage said ridge in a folded condition of said holder for enclosing said slide;
   spacer means integral with said sheet for supporting said slide in spaced relationship away from contact with said tray bottom and said cover top; and
   a window defined in one of said cover top and tray bottom, said window being closed in an original condition of said holder by a panel attached to said least one of said cover top and tray bottom by supporting means, said supporting means being preferentially rupturable under manual force applied to said panel for releasing said panel to open said window.

6. The holder of claim 5 wherein said spacer means comprise small bumps integral with said tray bottom and positioned to contact marginal areas of the slide.

7. The holder of claim 5 wherein said spacer means comprise a partition extending between opposite side walls and across said cover top in said cavity, and side notches in said ridge structure for receiving said partition in a closed condition of said holder, said partition dividing said cavity into a first portion and a second portion, said partition cooperating with spacer elements on said tray bottom for holding said slide in said spaced relationship.

8. The holder of claim 5 wherein said spacer means include corner block elements formed at two corners of said cavity and corner notches in said ridge structure configured to receive said corner block elements in said folded condition of said holder, said corner blocks opposing spacer elements on said tray bottom for holding said slide therebetween in said spaced relationship.

9. The holder of claim 5 wherein said peripheral flange includes tab means on opposite edges of said sheet to provide a finger hold and facilitate manual separation of said cover and tray portions when opening said holder.

10. A unitary holder for a medical specimen slide formed from a single originally planar thin sheet of moldable material into a three dimensional structure wherein said sheet retains a substantially uniform thickness throughout said holder, said sheet divided along a hinge line into a tray portion and a cover portion;
   a hollow male ridge structure on said tray portion defining a tray recess dimensioned to receive the specimen slide, said ridge structure including an end cove for admitting a finger into contact with and edge of said slide;
   a concave shell formed in said cover portion defining a cavity including a cover top and adapted to mate onto said ridge structure in a folded condition of said holder for enclosing said slide;
   a partition extending between opposite side walls and across said cover top in said cavity, and side notches in said ridge structure for receiving said partition in a closed condition of said holder, said partition dividing said cavity into a first portion and a second portion, said partition cooperating with spacer elements on said tray bottom for holding said slide in said spaced relationship; and
   a window defined in said cover top in said second portion in overlying relationship with said identification bearing portion of a said slide placed in said tray recess, said partition also protecting said specimen bearing portion of a said slide from exposure to said window;
   said window being closed in an original condition of said holder by a panel attached to said cover top by supporting means, said supporting means being preferentially rupturable under manual force applied to said panel for releasing said pane to open said window.

* * * * *